United States Patent [19]

Rind

[11] Patent Number: 4,483,332
[45] Date of Patent: Nov. 20, 1984

[54] CONSTRUCTION AND METHOD FOR FORMING AN ORTHOPEDIC CAST AND METHOD OF PRODUCING THE CONSTRUCTION

[76] Inventor: Bruce Rind, 104-40 Queens Blvd.-20G, Forest Hills, N.Y. 11375

[21] Appl. No.: 455,361

[22] Filed: Jan. 3, 1983

[51] Int. Cl.³ .............................................. A61F 5/04
[52] U.S. Cl. .................................... 128/89 R; 128/90
[58] Field of Search ...................... 128/87 R, 89 R, 90

[56] References Cited

U.S. PATENT DOCUMENTS

| | | | |
|---|---|---|---|
| 2,651,302 | 9/1953 | Berry | 128/87 R |
| 3,110,307 | 11/1963 | Hamilton | 128/89 R |
| 3,186,405 | 6/1965 | Bailey et al. | 128/87 R |
| 3,375,822 | 4/1968 | Rose | 128/90 |
| 3,415,243 | 12/1968 | Sheldon | 128/90 |
| 3,563,234 | 8/1968 | Umstead | 128/90 |
| 3,631,854 | 1/1972 | Fryer | 128/90 |
| 3,643,656 | 2/1972 | Young et al. | 128/90 |
| 3,760,056 | 9/1973 | Rudy | 128/90 |
| 3,930,496 | 1/1976 | Gibbons | 128/90 |
| 3,935,355 | 1/1976 | Kuhn | 128/90 |
| 3,990,437 | 11/1976 | Boyden, Jr. et al. | 128/90 |
| 4,019,506 | 4/1977 | Eschmann | 128/90 |
| 4,060,075 | 11/1977 | Blomer et al. | 128/90 |
| 4,070,027 | 1/1978 | Kifferstein et al. | 128/90 |
| 4,143,655 | 3-1979 | Custer et al. | |
| 4,157,713 | 6/1979 | Clarey | 128/87 R |
| 4,238,522 | 12/1980 | Potts. | |
| 4,266,298 | 5/1981 | Graziano | 128/89 R |
| 4,306,549 | 12/1981 | Canie | 128/90 |
| 4,378,009 | 3/1983 | Rowley et al. | 128/87 R |
| 4,393,867 | 7/1983 | Baron | 128/89 R |

Primary Examiner—C. Fred Rosenbaum
Assistant Examiner—C. W. Shedd
Attorney, Agent, or Firm—Spring, Horn, Kramer & Woods

[57] ABSTRACT

A construction and method for forming an orthopedic cast and method of producing the construction, wherein a portion of the body is surrounded with a flexible network of non-porous tubing substantially devoid of air and having at least one inlet. A flowable fluid is injected into the tubing through the inlet to render the network substantially rigid and the tubing is releasably retained in place until the network becomes rigid.

19 Claims, 21 Drawing Figures

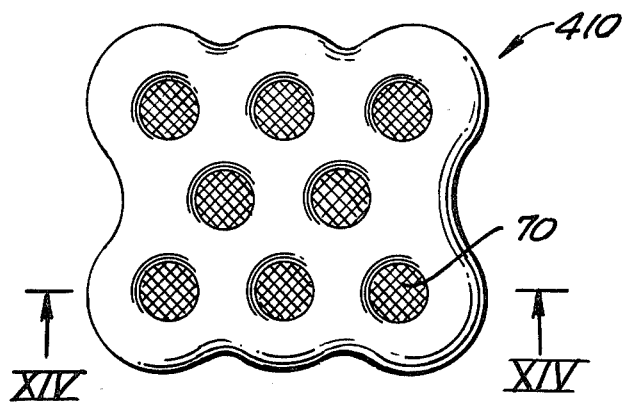
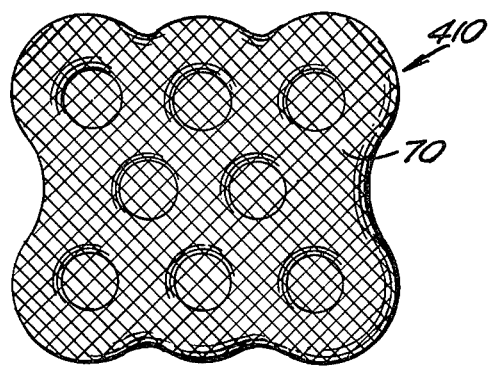
FIG.14a  FIG.14b
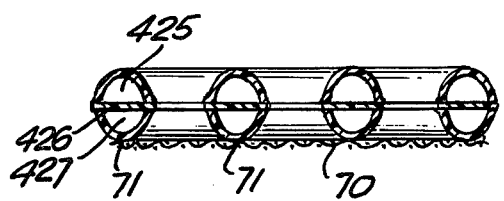
FIG.14c
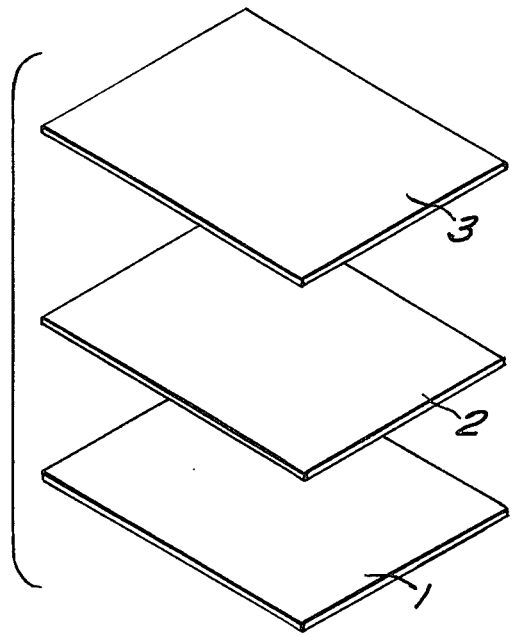
FIG.15
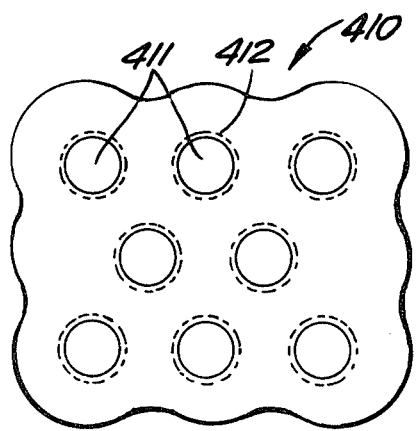
FIG.16

CONSTRUCTION AND METHOD FOR FORMING AN ORTHOPEDIC CAST AND METHOD OF PRODUCING THE CONSTRUCTION

BACKGROUND OF THE INVENTION

The present invention relates to a construction and method for forming an orthopedic cast and a method of producing the construction.

Plaster of paris has long been used for the fabrication of orthopedic casts. Casts of this type are generally heavy, bulky and easily broken. Moreover, because the material is sensitive to water and underpadding attracts or absorbs water, it is not possible to wash the cast and due to the fact that the material is opaque, it is impossible to allow any direct viewing of the skin absent the removal thereof.

Attempts to reduce the weight and bulk of orthopedic casts have resulted in the use of plastic material to construct same, for example, as shown in U.S. Pat. Nos. 4,238,522 and 4,143,655. The resulting orthopedic cast made from the materials disclosed therein still have many of the disadvantages of the plaster of paris casts due to the manner and form form in which the plastic material is used.

SUMMARY OF THE INVENTION

The object of the present invention is to eliminate the disadvantages of prior art orthopedic casts and to provide a construction and a method for forming orthopedic casts in accordance therewith.

These and other objects of the present invention are achieved in accordance with the present invention by a construction for forming an orthopedic cast which comprises a network of non-porous, preferably plastic tubing substantially devoid of air and having at least one inlet means receptive of a charge of flowable fluid for rendering the network substantially rigid. In a preferred embodiment, the flowable fluid is a charge of flowable and hardenable material such as a resinous material, acrylic plastic or epoxy which hardens in approximately 5-10 minutes. The flowable fluid may also be one which does not harden by itself, but reacts with a substance within the tubing to render the network rigid. The surface of the plastic tubing which abuts the body during the formation of the cast, preferably has cushioning means thereon which preferably comprises a sponge base.

In a preferred embodiment of the present invention, the network comprises double lumen tubes with one lumen abutting the portion of the body to be held in the cast being receptive of a nonhardening fluid such as air and the other lumen being receptive of the charge of hardenable material. The plastic material is preferably polypropylene or polystyrene.

In accordance with the method of the present invention, a portion of the body to be held immobile is surrounded with the network of plastic tubing and the tubing is filled with the charge of flowable and hardenable material and releasably retained in place until the material hardens. Where a double lumen network is used, the lumen holding the nonhardenable fluid is at least partially filled while the hardenable material is hardening and thereafter the volume of the nonhardening fluid may be adjusted.

The advantages of the present invention are numerous and significant. Because the network of tubing can be made of plastic materials such as polyethylene and polypropylene, it can be clear so that the portion of the body to be surrounded can be viewed during the initial fitting of the cast.

The network pattern of the tubing which is preferably net-like in appearance to permit biaxial stretching both vertically and horizontally. Alternatively the network pattern can be either a lattice-like pattern or quadrille to permit biaxial stretching along diagonal axes.

It can also be seen that the plastic material can be different colors for color coding the casts or to improve the appearance thereof when used for children, etc.

The fact that the tubular network can have a soft base either by means of the sponge or the double lumen fluid filled base, eliminates the need for an underpad and allows ventilation through the pores. Moreover, the plastic material is easily washable and readily driable.

Another advantage is the fact that preshaping is possible, that is the tubular network can be formed into a glove-like configuration or an angle or knee brace tube.

The use of the double lumen tubular network makes it possible for the underside of the tubular network to act as an inflatable pad which allows variable adjustment of the support to the limb and which is self-equilibrating. When the hardenable material finally hardens, the fluid-filled lumens give uniform circumferential pressure to the fracture site thus providing pressure which is always automatically equilibrated and remains so even while providing ventilation. The uniform circumferential hydrostatic pressure keeps the bone or bones in place while healing and uniformity is important to avoid pressure spots leading to sores.

In this vein, if it is necessary to cover the holes in the network, a net or mesh can be used below the tubular network to cover the holes and provide an even more uniform hydrostatic pressure.

It can be seen that after the material hardens, the pressure in the double lumen network can be adjusted. In this way, the tubes can be temporarily deflated after some healing has taken place to allow washing or rinsing under the cast or can be inflated to provide more pressure on the portion of the body that is surrounded by the cast.

It can be also seen that while the hardenable material is hardening, if one pinches one or more axial lines along the length of the cast, cutting and bending lines can be provided which, during use of the cast do not provide any instability in support, but upon desiring to remove the cast, provide an easy and effective way of removing the cast. The pinching can be carried out by laying a plastic tube along the length of the cast and wrapping it with an elastic bandage until the cast hardens.

The double lumen tubular network also provides means by which with the provision of an exit port, the network can be flushed with warm or cold fluid in order to heat or cool the limb surrounded by the cast if necessary. Moreover, the second lumen can be filled with a viscous fluid which acts as a damping or shock absorbing mechanism if such is desired.

Further in accordance with the present invention, a preferred method of producing the construction comprises disposing at least two plastic sheets in superposition, joining the sheets to form a network of interconnected tubular passages and removing the plastic between adjacent passages. In order to provide the double lumen tubular network, three sheets are disposed in superposition with the outer sheets joined to the intermediate sheet.

The network can be fiber reinforced by disposing at least one layer of fibers between the plastic sheets and inlet and outlet means can be provided by placing a valve between the sheets and joining same to be in communication with the tubular passages during the formation of the network.

Another advantage is that the construction is self-contained and can be used in any location.

These and other advantages and features of the present invention will be seen in more detail with reference to the following detailed description in conjunction with the attached drawings:

BRIEF DESCRIPTION OF THE DRAWINGS

FIG. 14a is a top view of an alternative embodiment of the construction according to the present invention;

FIG. 14b is a bottom view of the embodiment of FIG. 14a;

FIG. 14c is a sectional view along line XIV—XIV in FIG. 14a;

FIG. 15 illustrates the method of producing the construction of FIG. 16; and

FIG. 16 is a portion of a network formed according to the method of the present invention.

DETAILED DESCRIPTION OF THE INVENTION

Figure 1:
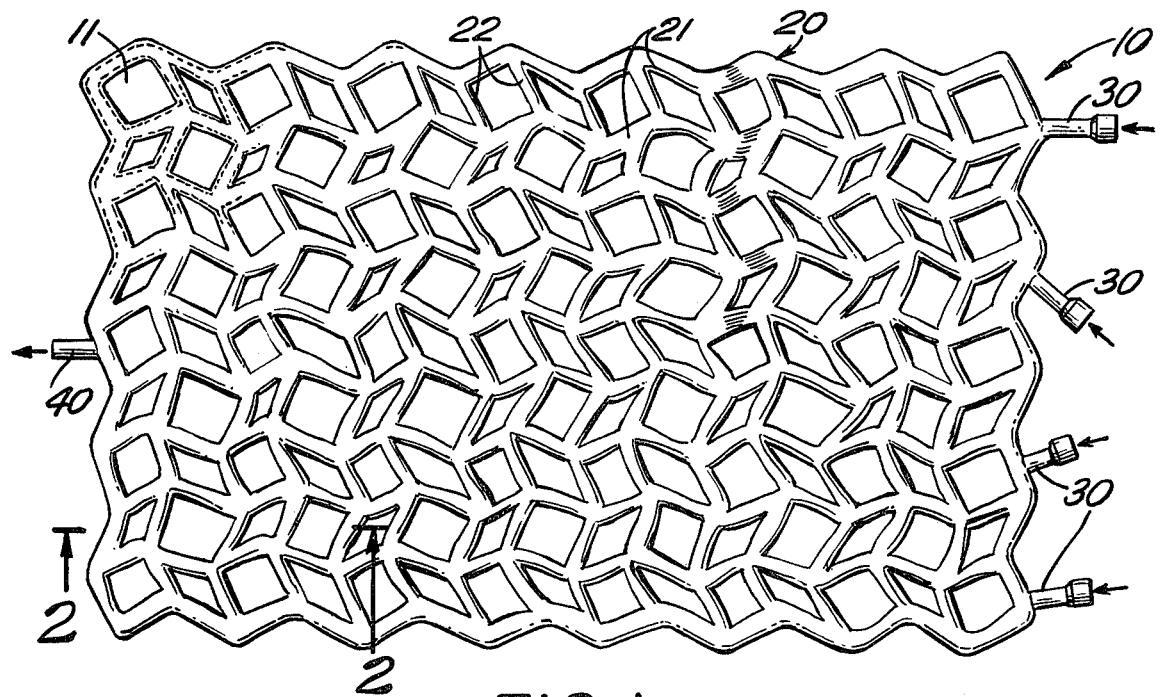
FIG. 1 is a top view of the construction according to the present invention.

Referring now to FIG. 1, the construction according to the present invention comprises a network 10 of tubes 20 including generally horizontal extending tubes 21 and generally vertically extending tubes 22. The network 10 is of a net-like configuration with holes 11 between horizontal and vertical tubes to permit stretching in the horizontal and vertical directions as well as along the diagonals.

Figure 1A:
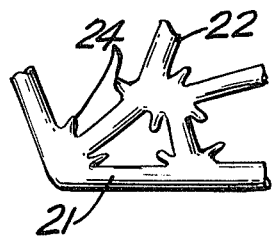
FIG. 1a is a detail of the construction of FIG. 1.

As shown in FIG. 1a, the network preferably comprises extra material 24 at the juncture of the tubes 21 and 22 so as to allow bending at the joints and minimize kinking the tubes.

The network of tubes 20 is constructed so that all of the tubes are in fluid communication with each other and in order to provide a fluid inlet thereto, at least one inlet valve means 30 is provided. The network may also be optionally provided with an outlet valve 40 for the purposes which will be explained hereinafter.

Figure 2:
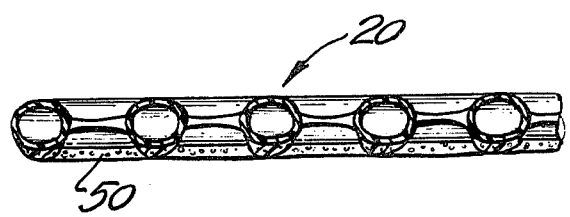
FIG. 2 is a sectional view along line 2—2 in FIG. 1.

FIG. 2 shows the cross section of the tubing of FIG. 1 in one preferred embodiment. The tubing 20 is a single lumen type and is shown in the inflated condition. The network when originally provided for use in constructing a cast, is devoid of any air in the tubing so as to make the input of a fluid much easier.

In use, a hardenable material such as a resin is input into the input valves 30 in liquid form so as to completely fill all of the tubing of the network. Alternatively, the tubing can have a reactable substance therein, such as the polymers disclosed in U.S. Pat. No. 4,143,655 and a reaction fluid such as warm water can be input into the tubing to initiate the hardening process. Prior to hardening, the network is wrapped around the portion of the body to be immobilized and retained in place by suitable means while the material hardens. Upon hardening, a suitable cast has been formed. It can be seen that due to the net-like configuration of the network 10, the cast can be initially stretched either in the horizontal or vertical directions when initially placed around the portion of the body to be immobilized so as to conform to the contour thereof and upon hardening, will not return to its original shape.

FIG. 2 also shows another feature of the invention, that is a sponge or soft material 50 on the underside of the tubing which contacts the body during the formation of the cast. The material 50 forms a cushion between the body and the hardened material in the tubing.

Figure 3A:
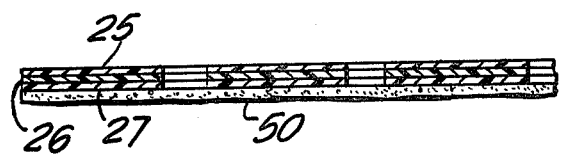
FIG. 3a is a sectional view of an alternative embodiment of the network of FIG. 1.
Figure 3B:
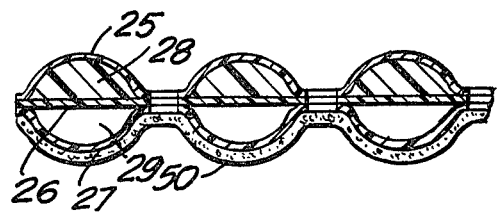
FIG. 3b is a sectional view of the FIG. 3a embodiment with the tubes inflated.

FIGS. 3a and 3b illustrate an alternative embodiment of the present invention wherein double lumen tubes are used to form the network 10. FIG. 3a shows the tubing in a collapsed condition and FIG. 3b shows the tubing in the inflated or filled condition. In this case, each lumen has at least one input valve. The tubing is formed from three elements 25, 26 and 27 which are superposed and joined at the edges thereof.

In use, the network of double lumen tubes has the lower lumen, that is the one closest to the body, at least partially filled with air 29. The upper lumen is filled with the hardenable flowable liquid material 28. Before hardening, the network is wrapped around the portion of the body and retained in place and the plastic material 28 is allowed to harden. Upon hardening, it is now possible to either deflate the lower lumen if the cast is too tight or inflate the lower lumen if the cast is too loose in order to obtain an optimal adjustment of the cast to the contour of the body. The lower lumen may also include cushioning material 50 as in the case of the single lumen tubing of FIG. 2.

Figure 4:
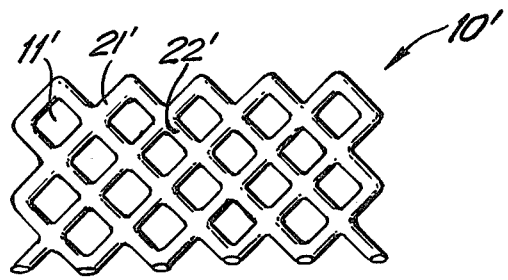
FIG. 4 is a top view of a portion of a network according to the present invention having a lattice pattern.

FIG. 4 shows an alternative configuration of the network 10' which is lattice-like in shape and allows for stretching in the vertical and horizontal directions. The network 10' includes the diagonally running tubular portions 21' and 22' and holes 11' therebetween.

Figure 5:
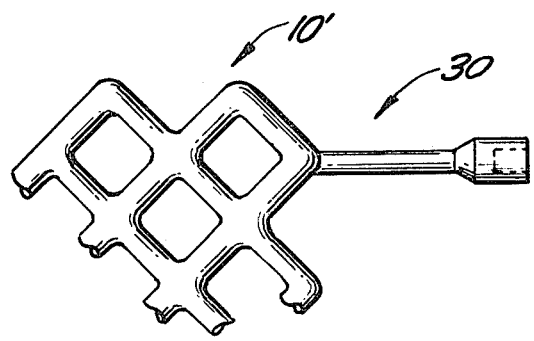
FIG. 5 is a portion of the embodiment of FIG. 4 showing the connection of an inlet valve.
Figure 6:
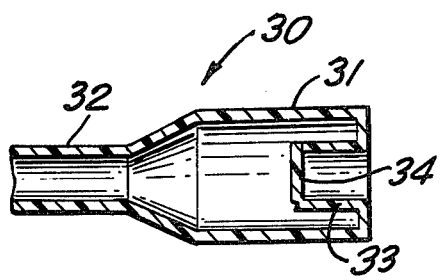
FIG. 6 is a sectional view of an inlet valve for the construction of FIGS. 1 and 4.
Figure 7:
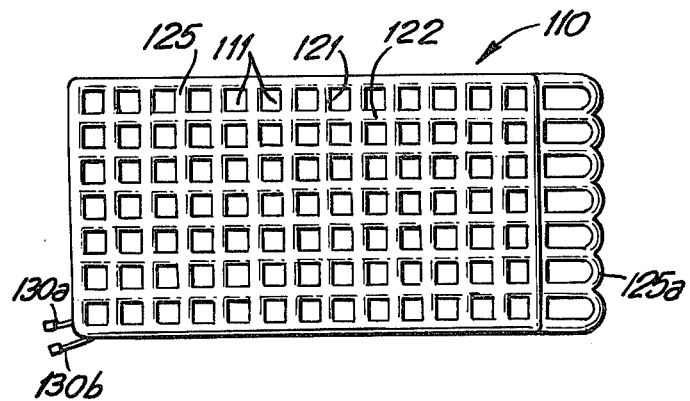
FIG. 7 is a top view of an alternative embodiment of the construction of the present invention having a quadrille.
Figure 8:
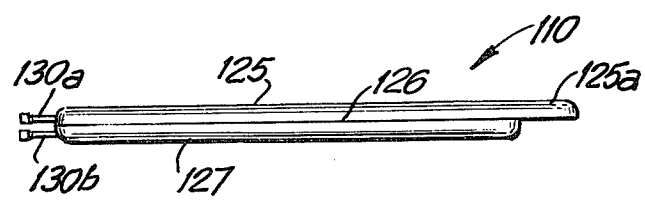
FIG. 8 is a side view of FIG. 7.
Figure 9:
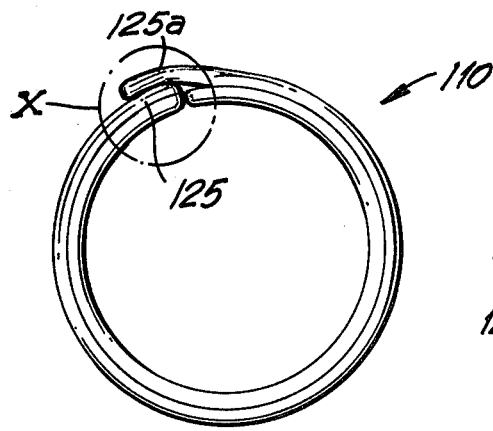
FIG. 9 shows the construction of FIG. 7 being assembled.

FIG. 5 shows the relationship of the inlet valve means 30' with respect to the network 10' of FIG. 4. The valve is shown in more detail in FIG. 6 wherein it includes the stem portion 32 integral with the valve body 31 and having a one-way flap valve 34 which is connected via a living hinge to the inlet forming portion 33. The valve member 34 prevents the flow of material outwardly of the valve 31 but permits the injection of hardenable fluid or air into the tubing.

Figure 13:
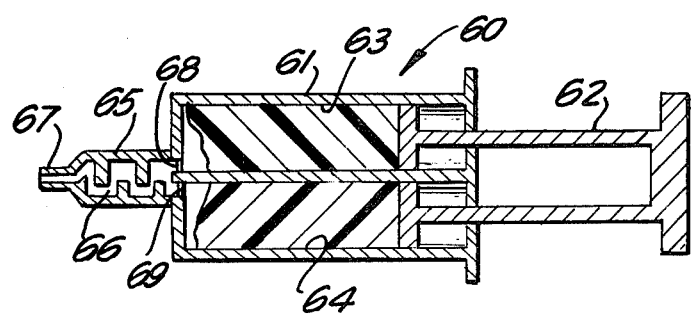
FIG. 13 is a sectional view of a double barrel syringe for inputting hardenable material into the network of FIGS. 1, 4 and 7.

FIG. 13 illustrates the type of syringe that can be used to inject the flowable material into the network via valve 30. The tip 67 of syringe 60 fits into the receiving portion 33 of valve 30 and pushes the hinged valve member 34 out of the way enabling the injection of material therein. As soon as the syringe tip 67 is removed, material is prevented from flowing out of the valve 30 by the valve member 34.

The double barrel syringe 60 shown in FIG. 13 is an expedient way of inserting the hardenable material into the network without having to first mix the components of the material. The syringe 60 is provided with a tubular body 61 having two reservoirs 63 and 64 for holding the resin components. The piston mechanism 62 pushes the material through the mixing chamber 65 having the static mixing path 66 therein so that the resulting material will harden in time. It is also contemplated that one might mix the resins beforehand and insert same into a single barrel syringe and charge same into the network before the material has had a chance to harden.

In the syringe 60 of FIG. 13, membranes 68 and 69 are provided in order to keep the resin components from mixing prior to the desired time. These can be easily broken by the pressure exerted via the piston plunger 62.

FIGS. 7-10 show an alternative embodiment network 110 for forming an orthopedic cast. The network 110 has a quadrille form comprising horizontal tubular portions 122 ad vertical tubular portions 121 with holes 111 spaced throughout. It should be clear that this type of construction can be stretched in the diagonal directions.

Figure 10:
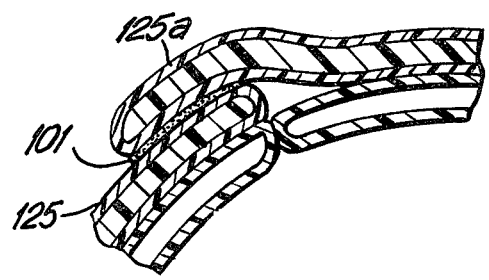
FIG. 10 is a detail of FIG. 9 shown within circle X.

The double lumen tubing of network 110 effectively forms an upper tubular portion 125 and a lower tubular portion 127 joined at central portion 126. Tubes 125 have inlet valve 130a for receiving the hardenable liquid material and tubes 127 have inlet valve 130b for receiving air. The tubular network portion 125 is configured to have overlapping portion 125a for the purpose of forming a connection when the network 110 is wrapped around a portion of the body. More specifically, as shown in FIG. 10, the network is wrapped around to form a cylindrical structure and the overhanging portion 125a overlaps the other end of portion 125. By spreading some of the hardenable material filling the tubes 125 or by using some other adhesive 101, the overlapping portion 125a can be connected to form a closed cast.

Figure 11:
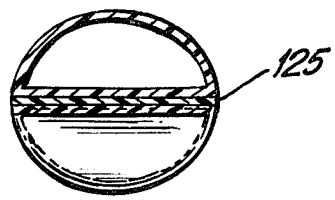
FIG. 11 is a sectional view of the tubing of FIG. 7 when pinched.

It may also be desirable during the hardening of the material to pinch the tubular portion 125 along one line of overlapping portion 125a and along another line opposite thereto as shown in FIG. 11. The pinching thereof will provide a portion which has no resin and thus is easily cut by a scissors or other instrument when it is desired to remove the cast. The provision of two pinch lines, enables one line to be cut and the other line to serve as a bendable hinge portion for two halves of the cast.

Figure 12A:
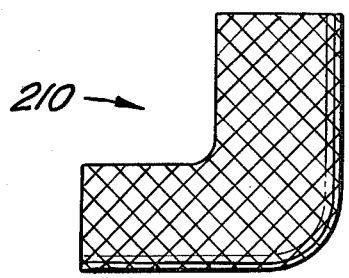
FIGS. 12a and 12b are planned views of preshaped casts according to the present invention.
Figure 12B:
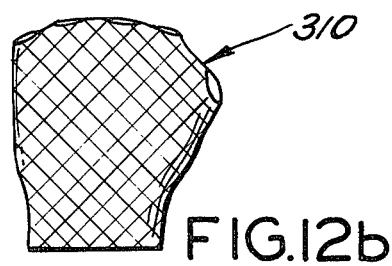

Because of the easy manner in which the construction of the present invention can be manipulated before the hardening material is inserted therein and hardens, it is clear that the construction can be preshaped for different uses. As shown in FIGS. 12a and 12b, the network can be performed into an L-shaped configuration 210 which can serve as an ankle cast or a knee cast or can be preshaped in the form of a glove 310 to act as a cast for the wrist or fingers.

FIGS. 14a-14c show another embodiment of the network according to the present invention which is not capable of being stretched, but which is easily constructed and usable as a cast. The network 410 has a regular pattern of holes and includes double lumen tubing including lumens 425 and 427 separated by member 426 and furthermore has a net or mesh 70 connected at points 71 to the tubing. By means of the mesh, the distribution of forces will be equalized so that when the lumen 425 is filled with hardenable material, it will leave a less pronounced pattern on the skin when the cast is removed.

FIGS. 15 and 16 illustrate the method by which the network 410 is constructed in accordance with the present invention.

The tubular network is first formed by providing three sheets 1-3 in superposition. A conventional dye is pressed against the three sheets simultaneously cutting out the holes 411 while forming a pressure induced joinder along line 412 which surrounds each hole and along the perimeter of the entire network. As a result, a network is formed wherein all of the tubes are in communication with each other for each lumen and the construction is devoid of any air upon assembly. The valves can be easily inserted during this construction by placing them between sheets 1 and 2 and sheets 2 and 3 and by heat sealing them also in place during the cutting of the holes and the sealing of the edges.

The netting or mesh 70 can also be added thereafter by heat sealing the mesh at points 71 to the finished network.

Moreover, the sponge base can be formed by applying a sponge sheet, having adhesive on one side, to the bottom sheet so that the adhesive holds same thereon. The sponge sheet is preferably applied before cutting the holes.

EXAMPLE

A network of the type shown in FIG. 4 constructed from polypropylene plastic is filled with fast hardening Ren Rapid TM clear epoxy and wrapped around the arm of a patient. The network is held in the wrapped position by tape and is allowed to harden for five minutes. After hardening the tape is removed.

It will be appreciated that the instant specification and claims are set forth by way of illustration and not limitation, and that various modifications and changes may be made without departing from the spirit and scope of the present invention.

What is claimed is:

1. A construction for forming an orthopedic cast comprising: a flexible network of non-porous tubing substantially devoid of air and having at least one inlet means receptive of a flowable fluid for rendering the network substantially rigid, wherein the network has two main faces including portions of the outer surface of the tubing and further comprising cushioning means disposed on one main face of the network and comprising a sponge base on the outer surface of the tubing.

2. The construction according to claim 1, wherein said flowable fluid comprises a charge of a flowable and hardenable material.

3. The construction according to claim 2, wherein the tubing comprises transparent plastic and the hardenable material is transparent.

4. The construction according to claim 1, wherein the plastic tubing comprises fiber reinforced plastic.

5. The constrction according to claim 1, further comprising means for retaining the network in place around a portion of the body while the network becomes rigid.

6. The construction according to claim 1, wherein the network is net-like to permit expansion thereof in all directions.

7. A construction for forming an orthopedic cast comprising: a flexible network of non-porous tubing substantially devoid of air and having at least one inlet means receptive of a flowable fluid for rendering the network substantially rigid, wherein the network has two main faces and wherein the tubing comprises double lumen tubes with one lumen facing one main face and the other lumen facing the other main face and wherein the inlet means includes at least one inlet for said one lumen receptive of said fluid and at least one inlet for said other lumen receptive of a non-hardening flowable fluid.

8. The construction according to claim 7, further comprising cushioning means disposed on said other main face of the network.

9. The construction according to claim 8, wherein the cushioning means comprises a sponge base on the outer surface of said second lumen.

10. The construction according to claim 7, wherein the network has an outlet for said other lumen to permit the circulation of a fluid therethrough.

11. A method for forming an orthopedic cast on a portion of the body, comprising the steps of:
surrounding the portion of the body with a flexible network of non-porous tubing substantially devoid of air and having at least one inlet, wherein the network has two main faces and the tubing comprises double lumen tubes with one lumen facing one main face and the other lumen facing the other main face, by disposing the other main face adjacent the portion of the body;
injecting a flowable fluid into the tubing through the inlet to render the network substantially rigid by at least partially filling said other lumen with a flowable non-hardening fluid and the one lumen with said flowable fluid; and
releasably retaining the tubing in place until the network becomes rigid.

12. The method according to claim 11, wherein the step of injecting comprises adjusting the volume of fluid in said other lumen after the material hardens.

13. The method according to claim 11, wherein the step of surrounding comprises preshaping the network to conform to the portion of the body.

14. A method for forming an orthopedic cast on a portion of the body, comprising the steps of:
surrounding the portion of the body with a flexible network of non-porous tubing substantially devoid of air and having at least one inlet;
injecting a flowable fluid into the tubing through the inlet to render the network substantially rigid;
releasably retaining the tubing in place until the network becomes rigid; and
pinching the network along a first axial line while the network becomes rigid to form a cutting line for the removal of the cast.

15. The method according to claim 14 further comprising the step of pinching the network along a second axial line opposite said first line to form a bending line for the removal of the cast.

16. A method of producing a construction for forming an orthopedic cast, comprising the steps of:
disposing at least two plastic sheets in superposition;
joining the sheets to form a network of interconnected tubular passages;
removing the plastic between adjacent passages; and
disposing a sheet of sponge material in superposition with the at least two sheets, prior to the steps of joining and removing.

17. The method according to claim 16, wherein the three sheets are disposed in superposition and the step of joining comprises joining the end sheets to the middle sheet.

18. The method according to claim 16, further comprising disposing at least one layer of fibers between the plastic sheets.

19. The method according to claim 16, further comprising placing a valve between the sheets and joining same in communication with the tubular passages.

* * * * *